United States Patent [19]

Lund et al.

[11] Patent Number: 4,820,452

[45] Date of Patent: Apr. 11, 1989

[54] BECHAMP REDUCTION OF DNS TO DAS USING $H_2SO_4$ AND TRACE OF HOAC

[75] Inventors: Richard B. Lund, Jackson; Glenn W. Brown, Wagarville, both of Ala.

[73] Assignee: Ciba-Geigy Corporation, Ardsley, N.Y.

[21] Appl. No.: 908,429

[22] Filed: Sep. 17, 1986

Related U.S. Application Data

[63] Continuation-in-part of Ser. No. 787,883, Oct. 16, 1985, abandoned.

[51] Int. Cl.$^4$ ............................................ C07C 143/62
[52] U.S. Cl. ..................................................... 260/510
[58] Field of Search ......................................... 260/510

[56] References Cited

U.S. PATENT DOCUMENTS

| | | | |
|---|---|---|---|
| 2,212,084 | 8/1940 | Straub et al. | 260/510 |
| 2,681,926 | 6/1954 | Lane et al. | 260/510 |
| 2,762,801 | 9/1956 | Hausermann | 260/249.6 |
| 3,472,842 | 10/1969 | Hausermann et al. | 260/240 |
| 3,506,657 | 4/1970 | Hausermann | 260/510 |
| 4,179,476 | 12/1979 | Franz et al. | 260/510 |
| 4,217,304 | 8/1980 | Albrecht et al. | 260/510 |

FOREIGN PATENT DOCUMENTS

| | | | |
|---|---|---|---|
| 2930754 | 1/1981 | Fed. Rep. of Germany. | |
| 48-42064 | 12/1973 | Japan | 260/510 |

OTHER PUBLICATIONS

Bechamp Reduction Process (Merck Index, 10th Ed. p. ONR-8) (1983).

*Primary Examiner*—Nicky Chan
*Attorney, Agent, or Firm*—Kevin T. Mansfield; Edward McC. Roberts

[57] ABSTRACT

A process for preparing bis-diaminostilbene dilsulfonic acid from bis-dinitrostilbene disulfonic acid by an improved Bechamp reduction process is disclosed. The process involves reduction with metallic iron in an acidic medium consisting of 0.033 to 0.27% of acetic acid and 0.38 to 0.76% of sulfuric acid in water at an oxidation-reduction potential (iron/thalamide electrode) in the range 140 to 270 millivolts.

3 Claims, No Drawings

BECHAMP REDUCTION OF DNS TO DAS USING H₂SO₄ AND TRACE OF HOAC

This is a continuation-in-part of application Ser. No. 787,883, filed Oct. 16, 1985, abandoned.

FIELD OF THE INVENTION

This invention relates to the production of bis-diaminostilbene disulfonic acid from bis-dinitrostilbene disulfonic acid by an improved Bechamp reduction process.

BACKGROUND OF THE INVENTION

Optical bleaches or brighteners are major chemical products. Many of these compounds are used in major amounts.

They are either added to the polymer component mixes before fiber and sheet formation or are coated unto the fibers, fabrics or pellicles formed therefrom. In addition fabric and textiles are also dyed with these products. Major amounts of these materials are also added to laundry washing compositions to impart brightening qualities to the laundry washed therein.

A major intermediate for the manufacture of many of these brighteners is 4,4'-diaminostilbene-2,2'-disulfonic acid. Optical bleaches and brighteners according to U.S. Pat. Nos. 2,762,801 and 3,472,842 are marketed by Ciba-Geigy Corp. under the trademark TINOPAL. Specifically, the optical brightener, disodium 4,4'-bis-[2''-phenylamino-4''-(N-methyl-β-hydroxyethylamino)-s-triazinyl-(6'')amino]-stilbene-2,2'-disulfonic acid is a thermally stable compound used in detergent, soap an similar laundry composition. These optical brightening washing compositions are used in commercial laundries and also in the home for the greater "whiteness" in white goods and also for enhancing the brilliance of the colored goods.

A major intermediate in this connection is the 4,4'-diaminostilbene-2,2'-disulfonic acid (DAS).

Diaminostilbene (DAS) has been prepared commercially by the Bechamp Reduction process (Merck Index, 10th Ed. pg. ONR-8) directed to the reduction of aromatic nitro compounds to the corresponding amines by iron or ferrous salts in aqueous acid.

The literature on this reaction indicatss acetic and hydrochloric acid to be commonly used. Until now DAS has been prepared from 4,4'-dinitrostilbene-2,2'-disulfonic acid by reduction with iron in aqueous acetic acid solution. While the literature indicates hydrochloric acid has also been used to activate the iron in Bechamp reductions it would not be useful for diaminostilbene production, as the corrosion rates are very high requiring the use of expensive corrosion resistant equipment such as glass lined reactors, filters and piping. Less expensive stainlss steel equipment is satisfactory for sulfuric acid service under the conditions used in the invention. Additionally, hydrochloric acid is more expensive than sulfuric acid.

In the reduction of 4,4'-dinitrostilbene-2,2'-disulfonic acid it is very important to maintain an acidic pH, most preferably in the range of 5-6 to avoid the formation of highly colored and undesirable sun yellow by-products. Acid is required in this invention for reaction control during the reduction as well as for activation of the powdered iron.

Tests to manufacture the diaminostilbene with sulfuric aacid have shown that sulfuric acid is less efficient than acetic acid in this process. The reaction rates are sufficiently lower to obviate any cost advantage lying in the use of the cheaper sulfuric acid. Using acetic acid, adjusted to the optimum pH of 5-6 by the addition of NaOH, the reduction is completed within about 30 minutes. With sulfuric acid alone substituted for the acetic acid, the reduction requires approximately 60 minutes under the same conditions. Attempts were made to approximate the pH and the salt containing conditions of the acetic-acid sodium-hydroxide process by the introduction of NaHSO₄, Na₂SO₄ and NaOH into the sulfuric acid. While slightly decreasing the reaction time to approximately 45 minutes, the production rate was still substantially slower than the acetic acid/sodium hydroxide process.

THE INVENTION

Applicants have discovered a method for obtaining 4,4'-diaminostilbene-2,2'-disulfonic acid by the Bechamp reduction wherein the acetic acid in the activation medium for the metallic iron is reduced to between 8 and 15% of the original acetic acid amount, the balance being sulfuric acid ($H_2SO_4$-93% or its equivalent as oleum). The purity and yields with this modified medium are the same as with acetic acid alone and the reaction proceeds to completion within the same or shorter reaction times. The amount of effluent needing treatment is reduced by using a lower amount of acetic acid. The sulfuric acid is considerably cheaper than acetic acid. Thus the process of this invention, in all its aspects offers considerable economies resulting, under commercial production schedules, in sizable annual savings.

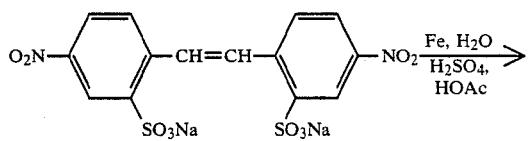

4,4'-Dinitrostilbene-2,2'-disulfonic acid
DNS
M.W. 430 (Free acid)

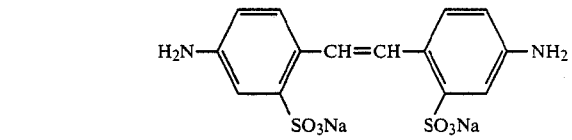

4,4'-Diaminostilbene-2,2'-disulfonic acid
DAS
M.W. 370 (Free acid)

The reduction medium is prepared initially as a slurry of finely divided iron filings or cast iron in about one third of the total reaction water. This slurry is initially activated by adding the total amount of the acetic acid (about 0.2% based on the DNS charge or 0.1% of the iron charge and an equal amount of sulfuric acid (93%). The reduction medium is activated by heating the acidified slurry to 95°–100° C. The degree of activation is checked by an oxidation reduction potential electrode (cast iron/thalamide) to an oxidation-reduction potential (ORP) of 130–140 millivolts. If the valee is greater than 140 it can be adjusted down by the addition of small amounts of mixed acids. To this activated slurry is added a slurry of the full amount of 4,4'-dinitro-2,2'-disulfonic acid suspended in the rest of the water and sulfuric acid. (The water is added to form a 15–20% wt/wt slurry of DNS). The feed rate of the DNS slurry to the agitated activated iron mixture is controlled so a to maintain the oxidation-reduction potential within the range 140 to 270 mv. The DNS feed is completed in about 30 minutes. The agitation is reduced after reaction is complete.

Upon completion of the reaction, the oxidation reduction potential should again be at about 140–150 mv. The reaction mass is checked for completion by spot testing with 10% NaOH solution. If the spot test is positive (pink, red or orange) the reaction mass is held for several minutes until the mixture tests negative. When the test is negative, agitation is reduced to permit the unreacted iron to settle out. The supernatant solution of the product is removed.

This solution, after adjusting to pH 10 with NaOH and filtration to remove all iron, may be used directly in subsequent synthesis of disodium 4,4'-bis-[2''-phenylamino-4''-(N-methyl-$\beta$-hydroxy-ethylamino)-s-triazinyl-(6'')-amino]-stilbene-2,2'-disulfonic acid or it may be crystallized by adding NaCl and the DAS precipitaee collected by filtration.

Thus the process of this invention resides in the utilization of a reduction medium containing about 0.2 to 1.2% by weight of acetic and sulfuric acfds, preferably about 0.64%. The concentration of acetic acid in the acidic Bechamp reduction medium is in the range 0.02 to 0.27%, preferably about 0.066% with the balance of the acid content being sulfuric acid (0.18 to 1.18% by weight, preferably about 0.57%).

The reducing agent is used in substantial excess. The unused iron is recycled. The iron used is preferably ground cast iron but other finely divided sources of metallic iron e.g. iron filings, capable of being activated in acidic solutions may be used. The test for sufficient activation capability is the xxidation-reduction potential of the iron slurry at 100° C. in the acid medium. The ORP should preferably be in the range 130–140 millivolts. Pyrophoric grades of iron powder should be avoided as they are difficult to wet and present fire and explosive hazards.

The DNS should constitute 8–20% by weight of the total reaction mixture and preferably 17% by weight (of the total reactant mass) should be of DNS (100%).

The reaction is initiated at about 100° C. When the DNS is added to the reducing slurry at the rate controlled by the ORP of 140 to 270 mv, the temperature of the reaction mixture is self-sustaining at about 100° C. $\pm 15°$.

The spot test indicates completion of the reaction within 30 minutes or less after completion of the addition of the reactants.

Within the stated proportion of acetic acid to sulfuric acid i.e. 8–15 parts to 92 to 85 parts respectively, the reaction is economically completed in 20 to 30 minutes at the indicated oxidation reduction potentials.

The reduction of DNS to DAS runs to completion yielding an excellent product of substantially 99%+purity in yields exceeding 96%.

The sulfuric acid may be used as the 93% concentration or at other weaker or stronger concentrations provided an equivalent amount of acid is present. Depending on availability it is often economical to use oleum 20 or 30. These refer to solutions of $SO_3$ in sulfuric acid and indicate the percentage of $SO_3$ dissolved in the acid.

The invention will be more fully described in examples which follow. These examples detail the invention practices preferred depending on varying economics, batch size, semibatch practice and practical ranges of the invention.

Each is preferred within its scope but art-recognized equivalent materials and operating conditions may be used without departing from the tenor of the invention and its proper metes and bounds.

DETAILED DESCRIPTION OF THE INVENTION

Example 1

Lab Scale

A two vessel set up was prepared comprising (a) a one liter three-neck, bottom outlet glass flask with agitator, marked at the 775 capacity level for holding and feeding the DNS slurry; and (b) a two liter stainless steel reducer-kettle equipped with a dual 8-blade turbine agitator, thermoeter, reflux condenser, DNS feed from a) above, an oxidation-reduction potential electrode (cast-iron/thalamide) millivoltmeter therefor, and a heatigg mantle. Meters and electrodes are provided for checking the pH in both vessels and for following the Redox (oxidation reduction) potential in the reducer.

The DNS feed flask is charged with 154.0 gms of DNS (100%) (M.W. 430)=0.358 mole. Water is charged to the 775 ml level and then 9.5 gm of sulfuric acid (100% $H_2SO_4$) is introduced with strong agitation.

The reducer is charged with 200 ml of water and agitation is started. Powdered iron 100%, 355 gms is then introduced with high speed agitation. Heating is continued while 0.93 grams of $H_2SO_4$ (100%) and 0.25 gm of acetic acid are added to the slurry. (The pH should be less than 6.) Heating is continued to reflux (90°–100° C.) and the ORP is followed until the 140 MV level, at 90°–100° C., is reached.

While monitoring the ORP level to below 270 MV by the feed rate, the DNS slurry, from its vessel, is introduced into the reducer vessel. Charging at this ORP rate takes about 30–60 minutes with fast agitation. When charging of the DNS is completed, fast agitation of the contents is continued at reflux for about 15 minutes. The ORP should drop back to below 160 MV. At this time any heating is discontinued and the mass is permitted to cool below the reflux temperature. Completion of the reaction is followed by spo checks with NaOH. If the reaction is incomplete, the batch is held longer near the reflux temperature. Foaming of the mass is another indication of incomplete reaction. When the reaction is completed, the agitation is reduced to a minimum and the supernatent $DAS/Fe_3O_4$ is suction decanted from the excess of the heavier iron metal.

The separated $DAS/Fe_3O_4$ slurry is maintained at 80°–90° C. with agitation and 50% NaOH is slowly introduced until the pH reaches 10–10.5. The alkalized $DAS/Fe_3O_4$ slurry is then filtered through a Super Cel-coated Buchner funnel to separate the $Fe_3O_4$ from the soluble DAS. The $Fe_3O_4$ precipitate is washed with a small amount of water.

To crystallize the DAS filtrate, its volume is measurdd and 20 volume % of NaCl is slowly charged to the heated filtrate at 60°–80° C. Crystals will start to form. The batch is allowed to crystallize for about 30 minutes, cooled rapidly to 20°-25° C. and filtered. The specific gravity of the filtrate is checked. It should be 1.15 to 1.17. If less than 1.15, more salt should be added to the filtrate and it should be refiltered. Yields of DAS over 5 replications were all in excess of 96% of substantially pure DAS. This was verified by utilizing the resulting DAS in the synthesis of disodium 4,4'-bis-[2''-phenylamino-4''-(N-methyl-$\beta$-hydroxy-ethylamino)-s-triazinyl-(6'')-amino]-stilbene-2,2'-disulfonic acid according to U.S. Pat. No. 3,472,842. The product of this further synthesis was completely satisfactory for commercial use.

The procedure of Example 1 with variations in the ratios of acetic acid to sulfuric acid indicated that the therein recited proportions of these acids were essentially optimum with regard to cost of materials and reaction time. The amount of acetic acid could be raised to from 0.1 to 0.5 grams without significant effects on the cost, purity or reaction rates. Above 0.5 grams the cost factors were increased, below about 0.1 grams it was noted that greater times were required for completion of the reaction. Attempts to buffer the sulfuric acid, activating medium to pH 5.4–5.6 with NaOH, NaHSO$_4$ or NaCl were unsuccessful as the DAS yields with such buffers, about 90–94%, were economically unacceptable. The product purity was similarly undesirable.

Example 2

The lab scale process according to Example 1, was modified to permit semi-batch operation whereby the residual slurry of unreacted iron remaining after removal of the supernatent DAS/Fe$_3$O$_4$ is reutilized. The reduction reactor discharge apparatus is adjusted to leave a residual slurry (Fe°) volume of about 550 ml after removal of the supernatent liquid of Example 1. To the 550 ml agitated residue in the reducer, is charged 98 gm of iron powder. Heating is resumed and 1.0 gram of H$_2$SO$_4$ and 0.25 grams of acetic acid are added.

The pH should be less than 6 (5.6–5.8) and the ORP should again be within the range 130–150 MV at 90°–100° C. The DNS batch, prepared as in Example 1, and contained in DNS vessel a), is then added to the reducing reactor b) and the reduction procedure is completed. Over a series of 10 semi batches, yields of substantial pure DAS in excess of 96% yield were obtained.

Example 3

Semi-batch plant scale

Into a 2000 gallon slurry vessel, fitted with an agitator and a bottom discharge; was pumped a 17% wt./wt slurry of DNS (2,299 lbs) in 11,569 lbs of water. To this was added 12 gal. (167 lbs) of 93% H$_2$SO$_4$ (or an equivalent amount of oleum). The pH of the resulting slurry was in the range 1.5 to 2.0. The slurry was ready for feeding to the reducing reactor below.

A 3000 gal stainless reactor fitted with a steam heating jacket, a reflux column, an agitator and sampling ports was charged with 540 gal. of water (4,510 lbs) and 5,520 lbs of powdered iron. The agitated slurry was then heated to 80°–85° C. and 17 lbs of 93% H$_2$SO$_4$ (1 gal) and 16 lbs glacial acetic acid were charged. The thus activated mix was then heated to 95°–100° C. and held until the ORP reading (iron/thalamide electrode) was 130–140 MV. The pH was 5–6. The contents of the DNS slurry vessel was then introduced at a rate so that the ORP reading was less than 270. At the end of the addition, fast agitation was maintained until the ORP 140 indicating substantial completion of the reduction reaction. Completion was verified by spot test with 10% NaOH. (Absence of pink, red or orange color indicated completion.) The reduction was complete within 30 minutes after all the DNS had been added.

Agitation was reduced to a minimum to permit settling of the unreacted iron powder. The supernatant slurry was transferred from the reduction reactor leaving a heel of 850 gal. containing iron powder and aqueous acid at pH 5.6–5.8.

The transferred slurry is then neutralized to remove the Fe$_3$O$_4$ on a filtration apparatus. The filtrate is then used as an intermediate for further syntheses requiring 4,4'-diaminostilbene-2,2'-disulfonic acid of high quality.

To continue the quasi-batch feature, the heel remaining in the reducer is reheated and charged with 1,380 lbs of iron powder, 16 pounds of H$_2$SO$_4$ and 8 pounds of glacial acetic acid. When the mixture has reached 100° C. and the ORP is stabilized at about 130=140 MV, a charge of DNS slurry prepared as before is introduced into the reducer reactor and the reduction proceeds as before.

After thirty repetitions of the above noted quasibatch process, the overall yield was 96+% of high purity 4,4'-diaminostilbene-4,4'-disulfonic acid suitable for direct synthesis of disodium 4,4'-bis-[2''-phenylamino-4''-(N-methyl-$\beta$-hydroxy-ethylamino)-s-triazinyl-(6'')-amino]-stilbene-2,2'-disulfonic acid.

What is claimed is:

1. In the process for the Bechamp reduction of 4,4'-dinitrostilbene-2,2'-disulfonic acid to 4,4'-diamino-stilbene-2,2'-disulfonic acid by reduction with metallic iron in an acidic medium, the improvement which comprises conducting the reduction in an acidic medium essentially consisting of 0.02 to 0.27% of acetic acid and 0.18 to 1.18% by weight of sulfuric acid in water.

2. The process according to claim 1 wherein the reduction medium, consisting essentially of about 0.066% of acetic acid and 0.57% of sulfuric acid is adjusted to a pH 5.4 to 5.6.

3. The process according to claim 1 wherein the reduction in the acidic medium is carried out while maintaining the oxidation-reduction potential in the range of 140 to 270 millivolts as measured by an iron/thalamide electrode.

* * * * *